US010632255B2

(12) United States Patent
Hochman et al.

(10) Patent No.: US 10,632,255 B2
(45) Date of Patent: Apr. 28, 2020

(54) DRUG INFUSION DEVICE

(71) Applicant: Milestone Scientific, Inc., Livingston, NJ (US)

(72) Inventors: Mark N. Hochman, Great Neck, NY (US); Nathan J. Inkrote, Manasquan, NJ (US); Robert D. Boyer, Boonton, NJ (US); Maureen A. Mullins, Mercerville, NJ (US)

(73) Assignee: MILESTONE SCIENTIFIC, INC., Livingston, NJ (US)

( * ) Notice: Subject to any disclaimer, the term of this patent is extended or adjusted under 35 U.S.C. 154(b) by 228 days.

(21) Appl. No.: 15/433,252

(22) Filed: Feb. 15, 2017

(65) Prior Publication Data

US 2018/0228968 A1 Aug. 16, 2018

(51) Int. Cl.
*A61K 38/48* (2006.01)
*A61K 9/00* (2006.01)
(Continued)

(52) U.S. Cl.
CPC ........... *A61M 5/172* (2013.01); *A61K 9/0019* (2013.01); *A61K 38/4893* (2013.01);
(Continued)

(58) Field of Classification Search
CPC .......... A61M 5/168; A61M 2005/2013; A61M 5/172; A61M 2205/3334;
(Continued)

(56) References Cited

U.S. PATENT DOCUMENTS 3,867,934 A 2/1975 Ollivier
4,356,826 A 11/1982 Kubota
(Continued)

FOREIGN PATENT DOCUMENTS

DE 202005019430 2/2006
EP 0303824 2/1989
(Continued)

OTHER PUBLICATIONS

Initial Publication with ISR of WO 2018/152225 (Year: 2018).*
(Continued)

*Primary Examiner* — Bhisma Mehta
*Assistant Examiner* — William R Frehe
(74) *Attorney, Agent, or Firm* — Niels Haun; Dann, Dorfman, Herrell & Skillman

(57) ABSTRACT

A method and apparatus are provided for providing a plurality of injections from a fluid reservoir. The apparatus includes a fluid controller for controlling the flow of fluid from the fluid reservoir to a needle. An actuator selectively actuates the fluid controller to provide a dose of medicament from the fluid reservoir. The fluid controller also is configured to calculate the volume of fluid in the fluid reservoir required to provide a dose having a desired number of units of medicament for an injection. The apparatus may also include a detector configured to detect a characteristic indicative of the fluid pressure in the needle. The method includes selecting the number of units to be dispensed during an injection, automatically calculating the injection volume required to dispense the selected number of units based on the calculated unit volume and tracking the total number of units dispensed during a series of injections.

12 Claims, 8 Drawing Sheets

(51) Int. Cl.
  *A61M 1/00* (2006.01)
  *A61M 5/142* (2006.01)
  *A61M 5/168* (2006.01)
  *A61M 5/172* (2006.01)
  *G06F 19/00* (2018.01)
  *G16H 10/60* (2018.01)
  *A61M 5/42* (2006.01)
  *A61M 5/145* (2006.01)

(52) U.S. Cl.
  CPC ........ *A61M 1/0039* (2013.01); *A61M 5/1456* (2013.01); *A61M 5/14212* (2013.01); *A61M 5/14236* (2013.01); *A61M 5/16877* (2013.01); *A61M 5/427* (2013.01); *C12Y 304/24069* (2013.01); *G06F 19/3468* (2013.01); *G16H 10/60* (2018.01); *A61M 2202/203* (2013.01); *A61M 2205/13* (2013.01); *A61M 2205/14* (2013.01); *A61M 2205/18* (2013.01); *A61M 2205/332* (2013.01); *A61M 2205/3334* (2013.01); *A61M 2205/3379* (2013.01); *A61M 2205/3569* (2013.01); *A61M 2205/50* (2013.01); *A61M 2205/502* (2013.01); *A61M 2205/505* (2013.01); *A61M 2205/52* (2013.01); *A61M 2205/581* (2013.01); *A61M 2205/582* (2013.01); *A61M 2205/583* (2013.01)

(58) Field of Classification Search
  CPC .... A61M 2202/203; A61M 2205/3379; A61M 2205/50; A61M 2205/502; A61M 2205/505; A61M 2205/52; G06F 19/3468; G16H 10/60
  See application file for complete search history.

(56) References Cited

U.S. PATENT DOCUMENTS

| | | |
|---|---|---|
| 4,403,988 A | 9/1983 | Binard |
| 4,518,383 A | 5/1985 | Evans |
| 4,624,659 A | 11/1986 | Goldberg |
| 4,679,567 A | 7/1987 | Hanlon |
| 4,790,821 A | 12/1988 | Stines |
| 4,801,293 A | 1/1989 | Jackson |
| 4,893,630 A | 1/1990 | Bray, Jr. |
| 4,988,337 A | 1/1991 | Ito |
| 4,998,914 A | 3/1991 | Wiest |
| 5,100,390 A | 3/1992 | Lubeck |
| 5,267,565 A | 12/1993 | Beard |
| 5,269,762 A | 12/1993 | Armbruster |
| 5,295,967 A | 3/1994 | Rondelet |
| D348,101 S | 6/1994 | Poli |
| 5,378,231 A | 1/1995 | Johnson |
| 5,405,269 A | 4/1995 | Stupecky |
| D360,259 S | 7/1995 | Ijiri |
| 5,520,650 A | 5/1996 | Zadini |
| 5,611,778 A | 3/1997 | Brinon |
| 5,660,567 A | 8/1997 | Nierlich |
| 5,681,285 A | 10/1997 | Ford |
| 5,690,618 A | 11/1997 | Smith |
| D390,654 S | 2/1998 | Alsberg |
| 5,810,770 A | 9/1998 | Chin |
| D409,148 S | 5/1999 | Hirai |
| 5,902,273 A | 5/1999 | Yang |
| 5,954,701 A | 9/1999 | Matalon |
| 6,022,337 A | 2/2000 | Herbst |
| 6,024,576 A | 2/2000 | Bevirt |
| 6,120,457 A | 9/2000 | Coombes |
| 6,126,610 A | 10/2000 | Rich |
| 6,159,161 A | 12/2000 | Hodosh |
| D436,927 S | 1/2001 | Hogan |
| 6,200,289 B1 | 3/2001 | Hochman |
| 6,468,241 B1 | 10/2002 | Gelfand |
| 6,569,147 B1 | 5/2003 | Evans |
| 6,652,482 B2 | 11/2003 | Hochman |
| 6,695,806 B2 | 2/2004 | Gelfand |
| 6,705,990 B1 | 3/2004 | Gallant |
| 6,716,192 B1 | 4/2004 | Orosz, Jr. |
| 6,773,417 B2 | 8/2004 | Fitzgibbons |
| 6,786,885 B2 | 9/2004 | Hochman |
| 6,886,648 B1 | 5/2005 | Hata |
| 6,887,216 B2 | 5/2005 | Hochman |
| 6,942,637 B2 | 9/2005 | Cartledge |
| 7,022,072 B2 | 4/2006 | Fox |
| 7,198,602 B2 | 4/2007 | Eide |
| D556,910 S | 12/2007 | Reihanifam |
| 7,335,162 B2 | 2/2008 | Eide |
| 7,364,570 B2 | 4/2008 | Gerondale et al. |
| 7,395,214 B2 | 7/2008 | Shillingburg |
| 7,449,008 B2 | 11/2008 | Hochman |
| D600,644 S | 9/2009 | Leung |
| 7,604,602 B2 | 10/2009 | Roteliuk |
| 7,618,409 B2 | 11/2009 | Hochman |
| 7,635,338 B2 | 12/2009 | Eide |
| 7,641,637 B2 | 1/2010 | Gerondale et al. |
| 7,775,985 B2 | 8/2010 | Eide |
| D630,727 S | 1/2011 | Wittwer |
| 7,896,833 B2 | 3/2011 | Hochman |
| 7,922,689 B2 | 4/2011 | Lechner |
| D642,984 S | 8/2011 | Arai |
| 8,002,736 B2 | 8/2011 | Patrick |
| 8,016,763 B2 | 9/2011 | Eide |
| 8,079,976 B2 | 12/2011 | Patrick |
| 8,137,312 B2 | 3/2012 | Sundar |
| 8,142,414 B2 | 3/2012 | Patrick |
| 8,197,443 B2 | 6/2012 | Sundar |
| 8,256,984 B2 | 9/2012 | Fathallah |
| 8,262,584 B2 | 9/2012 | Eide |
| D669,096 S | 10/2012 | Katsura |
| D669,165 S | 10/2012 | Estes |
| 8,282,565 B2 | 10/2012 | Mahapatra |
| 8,398,564 B2 | 3/2013 | Eide |
| D679,379 S | 4/2013 | Katsura |
| 8,444,592 B2 | 5/2013 | Williams |
| 8,480,630 B2 | 7/2013 | Mudd et al. |
| D687,536 S | 8/2013 | Shafer |
| 8,545,440 B2 | 10/2013 | Patrick |
| 8,562,600 B2 | 10/2013 | Kirkpatrick |
| 8,684,947 B2 | 4/2014 | Eide |
| 8,764,668 B2 | 7/2014 | Roteliuk |
| 8,814,807 B2 | 8/2014 | Hulvershorn |
| 8,992,481 B2 | 3/2015 | Mudd et al. |
| 8,998,841 B2 | 4/2015 | Shen |
| D730,514 S | 5/2015 | Havron |
| 9,044,542 B2 | 6/2015 | Patrick |
| D734,475 S | 7/2015 | Ross |
| D736,370 S | 8/2015 | Bodwell |
| D741,811 S | 10/2015 | Solomon |
| 9,199,044 B2 | 12/2015 | Bangera et al. |
| 9,205,204 B2 | 12/2015 | Bangera et al. |
| 9,358,038 B2 | 6/2016 | Hulvershorn |
| 9,358,350 B2 | 6/2016 | Bangera et al. |
| D760,888 S | 7/2016 | Friedrich |
| D765,832 S | 9/2016 | Solomon |
| 9,443,446 B2 | 9/2016 | Rios et al. |
| 9,452,261 B2 | 9/2016 | Alon |
| 9,468,396 B2 | 10/2016 | Mahapatra |
| 9,504,790 B1 * | 11/2016 | Hochman ............... A61M 5/20 |
| 9,603,537 B2 | 3/2017 | Lechner |
| 9,642,534 B2 | 5/2017 | Mahapatra |
| 9,655,528 B2 | 5/2017 | Zhu |
| D801,519 S | 10/2017 | Sloss |
| D803,386 S | 11/2017 | Sloss |
| D803,387 S | 11/2017 | Kerwin |
| 9,888,881 B2 | 2/2018 | Hulvershorn |
| 9,901,679 B2 | 2/2018 | Shen |
| 9,956,341 B2 | 5/2018 | Hockman |
| 1,000,445 A1 | 6/2018 | Moskowitz |
| 1,011,767 A1 | 11/2018 | Luo |
| 1,022,018 A1 | 3/2019 | Hochman |
| D859,634 S | 9/2019 | Hochman et al. |
| 1,040,628 A1 | 9/2019 | Anand |
| 2002/0016567 A1 | 2/2002 | Hochman |

(56) References Cited

U.S. PATENT DOCUMENTS

| | | |
|---|---|---|
| 2002/0016569 A1 | 2/2002 | Critchlow |
| 2002/0022807 A1 | 2/2002 | Duchon |
| 2002/0143294 A1 | 10/2002 | Duchon |
| 2003/0014006 A1 | 1/2003 | Alexandre |
| 2004/0035743 A1 | 2/2004 | Tighe |
| 2004/0149282 A1 | 8/2004 | Hickle |
| 2004/0215080 A1 | 10/2004 | Lechner |
| 2005/0004513 A1 | 1/2005 | Beyerlein |
| 2005/0004514 A1 | 1/2005 | Hochman |
| 2005/0096593 A1 | 5/2005 | Pope |
| 2006/0122555 A1 | 6/2006 | Hochman |
| 2006/0247657 A1 | 11/2006 | Trieu |
| 2007/0038143 A1 | 2/2007 | Christensen |
| 2008/0058702 A1 | 3/2008 | Arndt |
| 2008/0103408 A1 | 5/2008 | Denton |
| 2008/0281265 A1 | 11/2008 | Hochman |
| 2009/0131832 A1 | 5/2009 | Sacristan Rock et al. |
| 2009/0149911 A1 | 6/2009 | Dacey, Jr. |
| 2009/0149912 A1 | 6/2009 | Dacey, Jr. |
| 2009/0171191 A1 | 7/2009 | Patrick |
| 2009/0210029 A1 | 8/2009 | Tsui |
| 2009/0221914 A1 | 9/2009 | Barrett |
| 2009/0326482 A1 | 12/2009 | Hochman |
| 2010/0022918 A1 | 1/2010 | Fujie |
| 2010/0030102 A1 | 2/2010 | Poston |
| 2010/0049270 A1 | 2/2010 | Pastore |
| 2010/0056932 A1 | 3/2010 | Roteliuk |
| 2010/0179488 A1 | 7/2010 | Spiegel |
| 2010/0274191 A1 | 10/2010 | Ting |
| 2011/0021905 A1 | 1/2011 | Patrick |
| 2011/0060229 A1 | 3/2011 | Hulvershorn |
| 2011/0087166 A1 | 4/2011 | Davis |
| 2011/0112511 A1 | 5/2011 | Singer |
| 2011/0120566 A1 | 5/2011 | Ohmi |
| 2011/0190596 A1 | 8/2011 | Hacker |
| 2011/0288481 A1* | 11/2011 | Mudd ............... A61M 5/14244 604/131 |
| 2011/0298628 A1 | 12/2011 | Vad |
| 2011/0301500 A1 | 12/2011 | Maguire |
| 2012/0022407 A1 | 1/2012 | Lechner |
| 2012/0083760 A1 | 4/2012 | Ledford |
| 2012/0101410 A1 | 4/2012 | Lechner |
| 2012/0232389 A1 | 9/2012 | Guzman |
| 2012/0259237 A1 | 10/2012 | Axelrod |
| 2012/0289819 A1 | 11/2012 | Snow |
| 2013/0041258 A1 | 2/2013 | Patrick |
| 2013/0053851 A1 | 2/2013 | Schmitz et al. |
| 2013/0131633 A1* | 5/2013 | Mudd ...................... A61M 5/19 604/506 |
| 2013/0261533 A1 | 10/2013 | Norkunas |
| 2014/0012226 A1* | 1/2014 | Hochman ............. A61M 5/168 604/506 |
| 2014/0121636 A1 | 5/2014 | Boyden et al. |
| 2014/0121637 A1 | 5/2014 | Boyden et al. |
| 2014/0207050 A1 | 7/2014 | Gonzalez |
| 2014/0221965 A1 | 8/2014 | Regittnig |
| 2014/0316268 A1 | 10/2014 | Kafiluddi |
| 2014/0343406 A1 | 11/2014 | Damjanovic |
| 2015/0283365 A1 | 10/2015 | Dacey, Jr. |
| 2015/0374929 A1* | 12/2015 | Hyde .................. A61M 5/3294 604/191 |
| 2016/0136363 A1* | 5/2016 | McClellan ........... A61M 5/427 604/506 |
| 2016/0228633 A1 | 8/2016 | Welsch |
| 2017/0106142 A1 | 4/2017 | Hochman |
| 2018/0064870 A1* | 3/2018 | Hochman ............. A61M 5/168 |
| 2018/0228968 A1* | 8/2018 | Hochman ............. A61M 5/172 |

FOREIGN PATENT DOCUMENTS

| | | |
|---|---|---|
| EP | 0538259 | 4/1993 |
| FR | 2628625 | 9/1989 |
| HU | P8806113 | 10/1990 |
| HU | P0204296 | 3/2003 |
| JP | 5042218 | 2/1993 |
| JP | 6007440 | 1/1994 |
| JP | 6142114 | 5/1994 |
| WO | 9725081 | 7/1997 |
| WO | 03000146 | 1/2003 |
| WO | 2010071416 | 6/2010 |
| WO | 2017066732 | 4/2017 |
| WO | 2018152225 | 8/2018 |

OTHER PUBLICATIONS https://www.dermaqueen.co.kr/, published prior to Feb. 15, 2017.
http://www.intronixtech.com/myoguide-system/, published prior to Feb. 15, 2017.
http://www.anteis.com/AestheticDermatology/injectionsystem.php, published prior to Feb. 15, 2017.
International Search Report and Written Opinion issued in International Application No. PCT/US16/63861 dated Mar. 6, 2017.
International Search Report and Written Opinion issued in International Application No. PCT/US16/57264 dated Mar. 22, 2017.
Usubiaga et al., "Epidural Pressure and Its Relation to Spread of Anesthetic Solutions in Epidural Space", Anesthesia and Analgesia, vol. 46, No. 4, pp. 440-446, 1967.
Husemeyer et al., "Lumbar Extradural Injection Pressures N Pregnant Women", British Journal of Anaesthesia, 52, pp. 55-59, 1980.
Paul et al., "Extradural Pressure Following the Injection of Two Volumes of Bupivacaine", British Journal of Anaesthesia, 62, pp. 368-372, 1989.
Hirabayashi et al., "Effect of Extradural Compliance and Resistance on Spread of Extradural Analgesia", British Journal of Anaesthesia, 65, pp. 508-513, 1990.
Abstract of: Vas, "A study of epidural pressures in infants", Pediatric Anaesthesia, 11 (5), pp. 575-583, 2001.
Lechner et al., "Clinical results with a new acoustic device to identify the epidural space", Anaesthesia, 57, pp. 768-772, 2002.
NL Search Report, NL 2002708, dated Oct. 9, 2009.
PCT International Prelminary Report on Patentability, PCT/NL2010/000061, dated Oct. 4, 2011.
PCT International Search Report, PCT/NL2010/000061, dated Aug. 23, 2010.
Abstract of: Bilbao et al., "Neurological complications associated with ultrasound-guided interscalene and supraclavicular block in elective surgery of the shoulder and arm. Prospective observational study in a university hospital", Rev Esp Anestesiol Reanim, vol. 60, No. 7, Aug.-Sep. 2013, pp. 384-391.
Cohen et al., "Functional deficits after intraneural injection during interscalene block", Regional Anesthesia and Pain Medicine, vol. 35, No. 4, Jul.-Aug. 2010, pp. 397-399.
Gadsden et al., "Opening Injection Pressure Consistently Detects Needle-Nerve Contact during Ultrasound-guided Interscalene Brachial Plexus Block" Anesthesiology, vol. 120, No. 5, May 2014, pp. 1246-1253.
Hadzic et al., "Combination of intraneural injection and high injection pressure leads to fascicular injury and neurologic deficits in dogs", Regional Anesthesia and Pain Medicine, vol. 29 No. 5 Sep.-Oct. 2004, pp. 417-423.
International Preliminary Report on Patentability issued in International Patent Application No. PCT/US16/57264 dated Apr. 17, 2018.
Kapur et al., "Neurologic and histologic outcome after intraneural injections of lidocaine in canine sciatic nerves", ACTA, Anaesthesiologica Scandinavica, vol. 51, 2007, pp. 101-107.
Liu et al., "Incidence of unintentional intraneural injection and postoperative neurological complications with ultrasound-guided interscalene and supraclavicular nerve blocks", Anaesthesia vol. 66, 2011, pp. 168-174.
Lupu et al., "Nerve expansion seen on ultrasound predicts histologic but not functional nerve injury after intraneural injection in pigs", Regional Anesthesia and Pain Medicine, vol. 35, No. 2, Mar.-Apr. 2010, pp. 132-139.
Reiss et al., "Nerve injury complicating ultrasound/electrostimulation-guided supraclavicular brachial plexus block", Regional Anesthesia and Pain Medicine, vol. 35, No. 4, Jul.-Aug. 2010, pp. 400-401.

(56) References Cited

OTHER PUBLICATIONS

Sites et al., "Incidence of local anesthetic systemic toxicity and postoperative neurologic symptoms associated with 12,668 ultrasound-guided nerve blocks", Regional Anesthesia and Pain Medicine, vol. 37, No. 5, Sep.-Oct. 2012, pp. 478-482.
Sites et al., "Characterizing novice behavior associated with learning ultrasound-guided peripheral regional anesthesia", Regional Anesthesia and Pain Medicine, vol. 32, No. 2, Mar.-Apr. 2007, pp. 107-115.
Steinfeldt et al., "Forced needle advancement during needle-nerve contact in a porcine model: Histological outcome", Anesthesia & Analgesia, vol. 113, No. 2, Aug. 2011, pp. 417-420.
Steinfeldt et al., "Histological consequences of needle-nerve contact following nerve stimulation in a pig model", Anesthesiology Research and Practice, vol. 2011, Feb. 2011, 9 pages.
Widmer et al., "Incidence and severity of complications due to femoral nerve blocks performed for knee surgery", The Knee, Nov. 2012, 5 pages.
International Preliminary Report on Patentability for PCT/US2013/045142 Filed on Jun. 11, 2013.
Ghelber et al., "Identification of the Epidural Space Using Pressure Measurement . . . ", Regional Anesthesia and Pain Medicine, vol. 33, No. 4, Jul.-Aug. 2008, pp. 346-352.
Official Action issued in U.S. Appl. No. 11/208,400 dated May 29, 2008, 10 pages.
Iff et al., "The Use of an Acoustic Device to Identify the Epidural Space in Cattle", The Veterinary Journal, 187 (2011) pp. 267-268.
Iff, Isabelle, et al., "The use of an acoustic device to identify the extradural space in standing horses", Veterinary Anaesthesia and Analgesia, 2010, 37, 57-62.
Lechner et al., "Clinical Results with the Acoustic Puncture Assist Device, a New Acoustic Device to Identify the Epidural Space", Anesthesia Analgesia, (2003) pp. 1183-1187.
Lechner et al., "Thoracic Epidural Puncture Guided by an Acoustic Signal: Clinical Results", European Journal of Anesthesiology, 21 (2004) pp. 694-699.
Lechner, T.J.M. et al., "The use of a sound-enabled device to measure pressure during insertion of an epidural catheter in women in labour", Anaesthesia, 2011, 66, pp. 568-573.
Tsui et al., "Reduced Injection Pressures Using a Compressed Air Injection . . . ", Regional Anesthesia and Pain Medicine, vol. 33, No. 2, Mar.-Apr. 2008, pp. 168-173.
Extended European Search Report issued in EP Application No. 13813314.5 dated Feb. 18, 2016.
Examination Report issued in Australian Patent Application No. 2013287174 dated Oct. 26, 2016.
Jonathan Dillon, "Embedded storage in disposable medical items"; Article posted on Aug. 1, 2011; https://www.electronicproducts.com/Digital_ICs/Memory/Embedded_storage_in_disposable_medical_items.aspx.
"Medical Device Sanity"; http://mdgoo.blogspot.com/2014/12/another-medical-device-supplier-with.html; published prior to Oct. 27, 2017.
Maxim Integrated Product Specification for DS28EC20 20Kb 1-Wire EEPROM; published prior to Oct. 27, 2017.
International Preliminary Report on Patentability issued in International Application No. PCT/US13/45142 dated Jan. 15, 2015.
Al-Aamri, et al., "Reliability of Pressure Waveform Analysis to Determine Correct Epidural Needle Placement in Labouring Women", Anaesthesia 2017, 72, pp. 840-844.
Cohen et al, "Epidural Block for Obstetrics: Comparison of Bolus Injection of Local Anesthetic with Gravity Flow Technique", Journal of Clinical Anesthesia, 9, 1997, pp. 623-528.
Cohen et al, "Extradural Block in Obstetric Patients: Review of Experience with Gravity Administration", Acta Anaesthesiologica Scandinavica, 35, 1991, pp. 676-679.
Dawkins, "The identification of the epidural space" Anaesthesia, vol. 18, No. 1, Jan. 1963, pp. 66-77.
McKendry et al., "Pressure Waveforms to Assess Epidural Placement: Is There a Role on Delivery Suite?", Anaesthesia, 72, 2017, pp. 815-820.
Ghia, et al, "Confirmation of Location of Epidural Catheters by Epidural Pressure Waveform and Computed Tomography Cathetergram", Regional Anesthesia and Pain Medicine, vol. 26, No. 4 (Jul.-Aug.), 2001, pp. 337-341.
Gong et al, "Pressure Waveform-Guided Epidural Catheter Placement in Comparison to the Loss-of-Resistance Conventional Method", Journal of Clinical Anesthesia, 26 (2014) pp. 395-401.
Hong et al, "Analysis of Epidural Waveform for Cervical Epidural Steroid Injections Confirmed with Fluoroscopy", An.md-journal.com, Hong and Jung Medicine (2018) 97:13, 4 pages.
Lennox et al, "A Pulsatile Pressure Waveform Is a Sensitive Marker for Confirming the Location of the Thoracic Epidural Space", Journal of Cardiothoracic and Vascular Anesthesia, vol. 20, No. 5 Oct. 2006, pp. 659-663.
Leurcharusmee et al, "Reliability of Waveform Analysis as an Adjunct to Loss of Resistance for Thoracic Epidural Blocks", Regional Anesthesia and Pain Medicine, vol. 40, No. 6, Nov.-Dec. 2015, pp. 694-697.
Suwa et al, "Pressure-Guided Method for Identification of the Epidural Space in Children", Anesthesiology, vol. 89, No. 2, Aug. 1998, pp. 546-548.
Hsu et al, "The Frequency and Magnitude of Cerebrospinal Fluid Pulsations Influence Intrathecal Drug Distribution: Key Factors for Interpatient Variability", www.anesthesia-analgesia.org, vol. 115, No. 2, Aug. 2012, pp. 386-394.
Wagshul et al, "The pulsating brain: A review of experimental and clinical studies of intracranial pulsatility", http://www.fluidsbarrierscns.com/content/8/1/5, 2011, 8:5, 23 pages.
Hettiarachchi et al, "The Effect of Pulsatile Flow on Intrathecal Drug Delivery in the Spinal Canal", Annals of Biomedical Engineering, vol. 39, No. 10, Oct. 2011, pp. 2592-2602.
Hilber et al, "A systematic review of the diagnostic accuracy of epidural wave form analysis to identify the epidural space in surgical and labor patients", http://www.minervamedica.it, Minerva Anestesiologica, Apr. 2019, 85(4), pp. 393-400.
Iff et al., "The Use of an Acoustic Device to Identify the Extradural Space in Standing Horses", Veterinary Anaesthesia and Analgesia, 37 (2010) pp. 57-62.
Hungarian Novelty Report for Application No. P 04 00176.
International Search Report and Written Opinion issued in International Application No. PCT/US18/31096 dated Sep. 10, 2018.
Ross et al., "Pressures of Injection in a Cadaver Model of Peripheral Nerve Blockade", Journal of Anesthesia & Clinical Research, 2014, vol. 5, Issue 10, 4 pages.
Product brochure "PAJUNK: NerveGuard Automatic system for injection pressure limitation" (XS200192B) dated Jan. 2017, 4 pages.
International Search Report & Written Opinion issued in International Application No. PCT/US13/45142 dated Sep. 10, 2013.
International Preliminary Report on Patentability issued in International Application No. PCT/US06/29091 dated Feb. 28, 2008.
Gadsden, et al., "High Opening Injection Pressure Is Associated With Needle-Nerve and Needle-Fascia Contact During Femoral Nerve Block", Regional Anesthesia and Pain Medicine, vol. 41, No. 1, Jan.-Feb. 2016, pp. 50-55.

* cited by examiner

DRUG INFUSION DEVICE

FIELD OF THE INVENTION

The present invention relates generally to the delivery of drugs, particularly to systems for subcutaneous injection/aspiration for drug delivery providing controlled metering and automatic delivery of a defined unit of a subcutaneous drug injection. In particular, the present invention provides a means and method of calculating, controlling, and monitoring fluid injections from a hypodermic needle.

BACKGROUND OF THE INVENTION

Injection devices and systems are known in the medical arts, for use in delivery or a prescribed medication that are used for therapeutic and cosmetic purposes. Several systems have been developed for the administration of such injectable agents used to treat any of a number of conditions including but not limited to a cosmetic condition (i.e., wrinkles, sagging skin), pain (i.e., migraine), neurologic disorders (i.e., idiopathic neuropathy), endocrine condition, metabolic condition (i.e., diabetes), neuromuscular disorder (i.e., cervical dystonia, blepharospasm), inflammation (i.e., arthritis, psoriasis), vascular disorder (i.e., varicose veins, rosacea), cancer, infection, etc. Injectable agents can include but not be limited to neurotoxins, subcutaneous volume enhancers (dermal fillers), insulin, antibiotics, hormones, chemotherapeutic, or biological agents. Often certain procedures require a series of injections of varying amounts to be injected into the patient. Determining the amount of each injection and monitoring the amount of fluid injected can be cumbersome for a medical professional. Additionally, patient discomfort can result if the medicament is injected at a high rate. Conversely, if the flow rate for each injection is too low, the overall procedure can be elongated leading to patient discomfort and wasted time for the medical professional. Accordingly, there exists a need for a system for providing a controlled series of precise injections at an appropriate rate along with the ability to automatically calculate the appropriate volume for each injection to provide the desired number of units of medicament. Additionally, there exists a need for a system that tracks the amount of medicament injected during a series of injections along with the placement of the injections.

SUMMARY OF THE INVENTION

In light of the foregoing, the present invention provides a device and method that enables a practitioner to administer a precise standardized unit dose of a drug. The present invention also provides a method and apparatus for recording the location of injection on an anatomic pictorial record that can be recorded, stored and printed. The present invention further provides a method and apparatus for calculating and generating a standardized unit drug dose from a reconstituted (or diluted) drug that can then be used as a standardized dose unit between different drugs, providing a means of recording the injection related to specific unit dose on an anatomic pictorial record.

According to one aspect, the present invention provides an apparatus for providing an injection. The apparatus includes a fluid reservoir for retaining a volume of medicament that includes a number of units of medicament in a volume of diluent and a fluid controller for controlling the flow of fluid from the fluid reservoir. A needle is in fluid communication with the fluid reservoir for injecting the medicament subcutaneously or intramuscularly into the patient. The apparatus may optionally include a detector configured to detect a characteristic indicative of the fluid pressure of the fluid in the needle. The apparatus also includes an actuator for selectively actuating the fluid controller to provide a dose of medicament from the fluid reservoir. The fluid controller may be configured to to calculate the volume of fluid in the fluid reservoir required to provide a dose having a desired number of units of medicament for an injection. Additionally, the apparatus may include an input device for inputting information regarding the desired number of units in the dose.

According to another aspect, the invention provides an electric motor for driving a drive element connected with a fluid reservoir to expel fluid from a reservoir. Optionally, the fluid reservoir comprises a syringe having a barrel and a plunger slidable within the barrel. The fluid controller may be configured to engage the plunger of the syringe.

According to another aspect, the present invention comprises an apparatus for providing an injection comprising a fluid controller for providing a dose of medicament having a desired number of units of medicament, wherein the apparatus includes actuator in the form of a manually actuable button for providing control signals to the fluid controller.

According to a further aspect, the present invention provides a drug delivery system that includes a fluid controller having a processor operable to track the number of units of medicament dispensed during a procedure based on the number of times an actuator is actuated and information regarding the number of units injected upon each actuation of the actuator.

According to yet another aspect, the present invention provides a drug delivery system having a visual display for displaying a portion of the anatomy into which a needle provides a series of injections. Optionally, the display may provide a record keeping interface for indicating the anatomical location of each of the series of injections. Additionally, the record keeping interface may indicate the number of units injected at each anatomical location.

According to a further aspect, the present invention provides a drug delivery system having a fluid controller that comprises an electronic controller wherein the controller is configured to compare the number of units injected during a series of injections with the number of units indicated during a record keeping interface.

According to another aspect, the present invention provides a drug delivery system having a fluid controller and a fluid pressure sensor in line with a needle for detecting a characteristic indicative of the fluid pressure in the needle.

According to a further aspect, the present invention provides a method for using a fluid control system to automatically dispense fluid to a hollow needle for a series of injections. The method includes the step of preparing a volume of medicament by mixing a volume of diluent in a container having a number of units of medicament and providing a fluid reservoir having a volume of medicament from the container. Data is input into the fluid control system regarding the volume of diluent in the container and the number of units of medicament in the container. The fluid control system automatically calculates a unit volume, wherein the unit volume is the volume of fluid in the fluid reservoir required to dispense a unit of medicament based on the step of inputting data. The number of units to be dispensed during an injection is selected. The fluid control system automatically calculates the injection volume, wherein the injection volume is the volume of fluid in the fluid reservoir required to dispense the select number of units based on the calculated unit volume. An actuator is actuated, wherein in response to the step of actuating the fluid control system expels the calculated injection volume from the fluid reservoir. The steps of selecting and actuating may be repeated a plurality of times. The method may also include the step of tracking the total number of units dispensed during the steps of selecting and actuating to determine the total number of units dispensed during a procedure.

According to another aspect, the present invention provides a method for automatically dispensing fluid to a needle and the method includes the step of providing a visual display for displaying a portion of the anatomy into which a series of injections are provided and creating an injection map by identifying the location of each injection and the number of units injected at each location. The location and number of units may be identified on the portion of the anatomy displayed on the visual display.

According to a further aspect, the present invention provides a method for automatically dispensing fluid to a needle and the method comprises the step of calculating the difference between the total number of units dispensed during the procedure and the total number of units identified for each injection identified during the creation of an injection map.

According to yet another aspect, the present invention provides a method for automatically dispensing fluid to a needle and the method includes the step of calculating the number of units of medicament in a fluid reservoir; and re-calculating the number of units of medicament remaining in the fluid reservoir after each step of actuating an actuator to dispense fluid from the reservoir.

According to a further aspect, the present invention provides an apparatus for providing an injection from a fluid reservoir. The fluid reservoir contains a volume of medicament that includes a number of units of medicament in a volume of diluent. A fluid controller controls the flow of fluid from the fluid reservoir. A needle is in fluid communication with the fluid reservoir for injecting the medicament into the patient. An actuator is provided for selectively actuating the fluid controller to provide a dose of medicament from the fluid reservoir. The fluid controller may be operable to calculate the volume of fluid in the fluid reservoir required to provide a dose having a desired number of units of medicament for an injection. The apparatus may also include an input device for inputting information regarding the desired number of units in the dose. Additionally, the input device may include a visual display screen for displaying a record keeping interface for indicating the anatomical location of each of the series of injections.

According to yet another aspect, the present invention provides an apparatus for providing an injection and the system may include a display providing a record keeping interface that indicates the number of units injected at each of a series of anatomical locations.

According to a further aspect, the present invention provides an apparatus for providing an injection that includes a fluid controller. The fluid controller may include a processor operable to track the number of units dispensed during a procedure based on the number of times an actuator is actuated and information regarding the number of units injected upon each actuation of the actuator. Optionally, the processor may be configured to compare the number of units injected during the series of injections with the number of units indicated in the record keeping interface.

BRIEF DESCRIPTION OF THE DRAWINGS

The foregoing summary and the following detailed description of the preferred embodiments of the present invention will be best understood when read in conjunction with the appended drawings, in which.

DETAILED DESCRIPTION OF THE INVENTION

Figure 1:
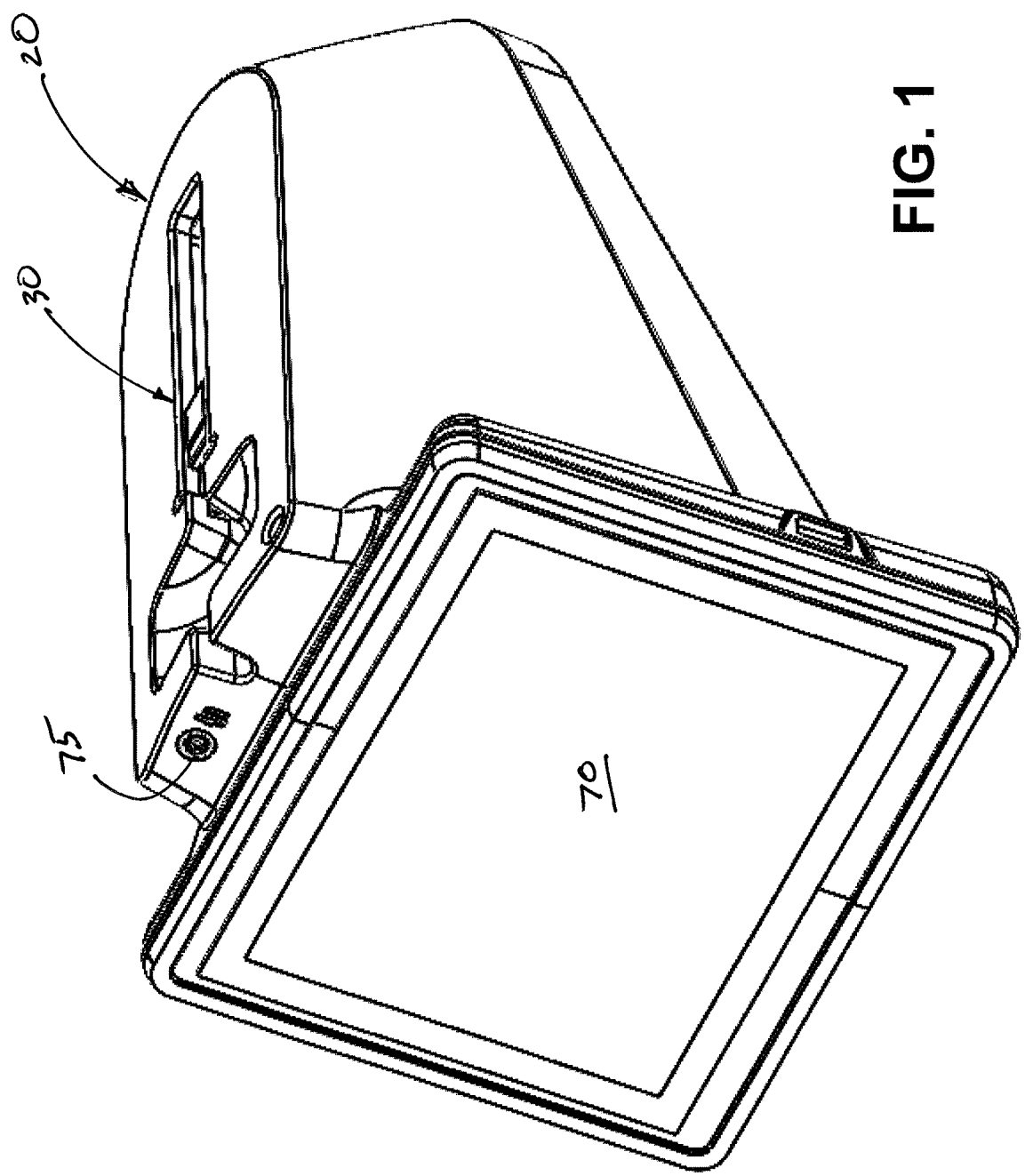
FIG. 1 is a perspective view of a drug infusion apparatus.

Referring now to the drawings, in general and to FIGS. 1-5 specifically, a drug infusion system is designated generally 5. The system 10 includes a computer-controlled drug delivery instrument 20, referred to as a drive unit. The drive unit 20 controls the flow of fluid from a fluid reservoir to an injection needle 120. The system 10 also includes a user interface 70 that allows the medical professional to customize the control of the fluid delivery as well as to audit the medical procedure and store a record of the details of the procedure.

Automated Fluid Delivery System

The system 10 includes a fluid delivery assembly 20 for providing a controlled flow of medication to an injection needle 120. The fluid delivery system is an automated system and in the present instance is a computer controlled fluid delivery system referred to as a drive unit 20.

Figure 2:
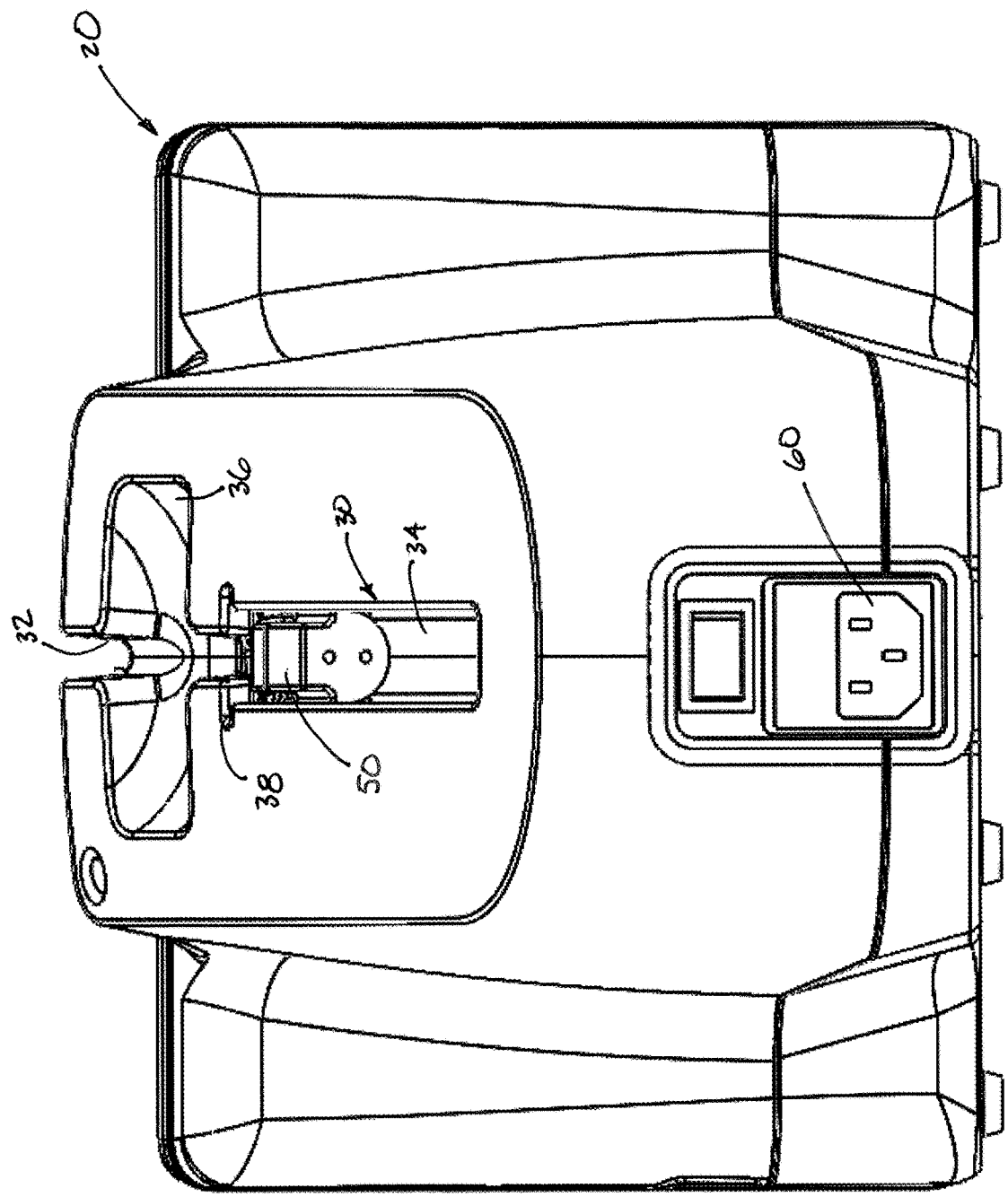
FIG. 2 is a rear view of the drug infusion apparatus illustrated in FIG. 1.
Figure 3:
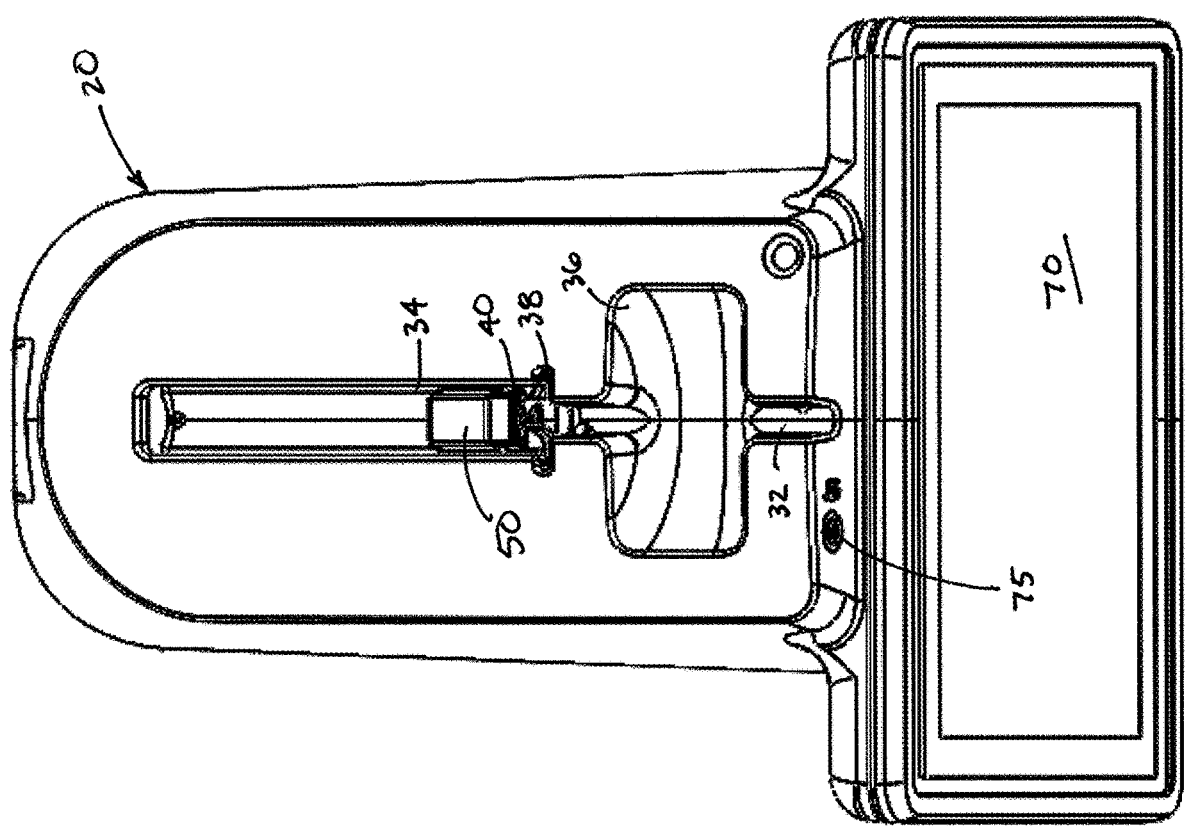
FIG. 3 is a plan view of the drug infusion apparatus illustrated in FIG. 1.

Referring to FIGS. 1-5, the drive unit is designed to work in connection with a fluid reservoir 90. For instance, the fluid reservoir may be a syringe 90. Accordingly, the drive unit 20 may be configured to accommodate a syringe. For instance, the drive unit 20 may include a cradle 30 configured to receive a barrel 92 and plunger 94 of a syringe. The cradle 30 may include an elongated slot 32 configured to receive the barrel 92 of the syringe 90. The slot 32 may have an open forward end as shown in FIGS. 1-2. In this way, the tip of the syringe 90 may protrude from the end of the slot 32. The cradle 30 further includes a plunger slot 34 that intersects the barrel slot 32 and is axially aligned with the barrel slot. The plunger slot 34 is configured to receive the plunger 94 of the syringe 90. In particular, the plunger slot 34 is substantially the length of the syringe plunger 94 so that the plunger slot can receive the length of the plunger when the plunger is extended from the barrel of the syringe. The cradle 30 may also comprise a transverse slot 38 configured to receive the flanges 96 of the syringe barrel 94. The transverse slot 38 engages the finger flanges 96 of the syringe to impede axial displacement of the syringe barrel 92 relative to the plunger 94. The drive unit 20 may also include a clamp 40 for releasably retaining the syringe 90 in the cradle 30. For instance, the clamp 40 may include one or more resilient elements that provide sufficient friction to impede ejection of the syringe from the cradle 30.

As shown in FIG. 1, the cradle 30 is elongated so that the cradle can receive the barrel 92 of the syringe and the plunger 94 when the plunger is withdrawn to the rearward end of the plunger barrel. More specifically, the cradle is longer than the maximum extended length of the syringe so that the syringe can be positioned in the cradle without engaging the plunger when the plunger is withdrawn to its maximum length from the barrel.

The drive unit 20 includes a drive element for displacing the plunger 94 in the cradle 30 relative to the barrel 92. The drive element can be any of a variety of linearly displaceable elements that can be accurately controlled. For instance, the drive element may include a drive screw, wherein rotation of the screw drives the plunger forwardly. In the present instance, the drive unit 20 includes a drive block 50 that engages the rearward end of the plunger 94. The drive unit controls the forward movement of the drive block 50 to control the flow of fluid from the syringe 90 to the needle 120. In particular, the drive block 50 is axially displaceable within the plunger slot 34 to drive the plunger relative to the barrel. Specifically, the drive unit 50 controls the advancement of the drive block 20 to advance the plunger to eject fluid from the syringe barrel 92. Similarly, the drive unit controls retraction of the drive block 50 (i.e. axial displacement in a direction opposite of the advancement) to withdraw the plunger from the barrel to aspirate the syringe. The drive unit 50 may further includes a retention element for providing a releasable connection between the plunger 94 and the drive block 50. For example, the drive unit may include a plurality of resilient fingers that engage the thumb pad of the plunger to connect the plunger with the drive block 50.

The drive unit 20 includes an electronic controller, such as a microprocessor, for controlling the operation of the drive unit in response to signals received from the user. The electronic controller controls the drive mechanism that drives the drive block to provide an injection. For instance, the drive mechanism may include an armature connected with the drive block 50. The drive unit may control an electric motor that drives the armature to drive the drive block.

The drive unit 20 may provide a variety of input mechanisms for the medical professional to provide input signals for controlling the operation of the drive unit. For instance, the drive unit may include one or more of a variety of input devices, including, but not limited to: manually actuable buttons, a keyboard, a mouse, a foot pedal, or a touch screen. The system also includes a display 70 so that the user can monitor the progress of the medical procedure as well as review information regarding the procedure. In the present instance, the display is a touch screen display 70 that allows the user to input data and various parameters to control the operation of the drive unit 20 during a procedure. Additionally, as discussed below, the drive unit 20 may include an input jack 75 for connecting an external control element that provides input signals to the drive unit 20. The input jack 75 may provide an electrical connection between the electronic controller of the drive unit and an external control element as described further below.

Injection Assembly

Figure 4:
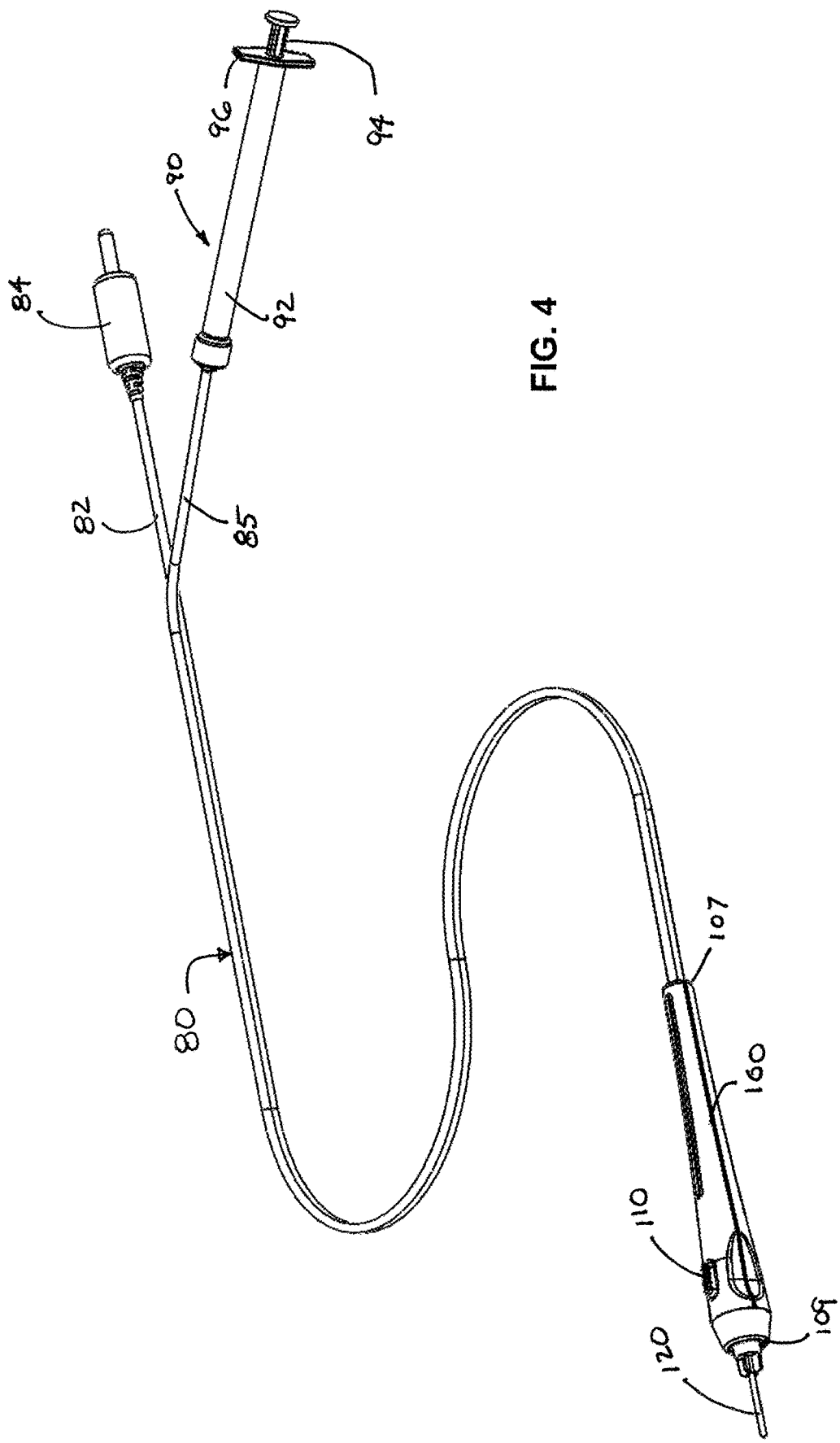
FIG. 4 is a perspective view of an injections assembly for use with the drug infusion apparatus illustrated in FIG. 1.

Referring to FIG. 4, the system 10 includes an injection assembly 80 cooperable with the drive unit 20 during a drug infusion procedure. The injection assembly includes a syringe 90, a handpiece 100, a fluid line 85 connecting the syringe with the handpiece and a cable providing an electrical connection between the handpiece and the drive unit 20. The assembly further includes a needle 120 releasably connected with the handpiece 100.

Various elements of the injection assembly may be disposable, such as the syringe 80, the fluid line 85, the handpiece 100 and/or the needle 120. Alternatively, the elements may be re-useable. Accordingly, various elements of the injection assembly are releasably connectable. For instance, the fluid line 85 may include a fluid connector at each end. The fluid-tight connectors may be any of a variety of connectors. One exemplary connector is a Luer connector. At the first end, the fluid connector sealingly connects with the syringe and at the second end, the fluid line sealingly connects with the handpiece 100. Alternatively, the fluid line 85 may be fixedly connected with the rearward end of the handpiece 100. In either embodiment, the handpiece 100 and the syringe are in fluid communication to provide a flow of fluid from the syringe to the handpiece.

The syringe 90 may be any of a variety of hypodermic syringes and the size may vary depending on the intended use. For instance, in one application the drive unit 20 may be used for cosmetic surgery to provide a series of facial injections. In such applications, the syringe may be a 1 cc volume syringe. The syringe 90 includes a barrel 92 for holding a volume of medicament and a plunger 94 slidable within the barrel to draw fluid into or eject fluid from the barrel. The syringe 90 preferably also includes flanges 96 projecting outwardly from the barrel. The flanges operate as finger flanges to facilitate displacement of the plunger into the barrel.

Figure 5:
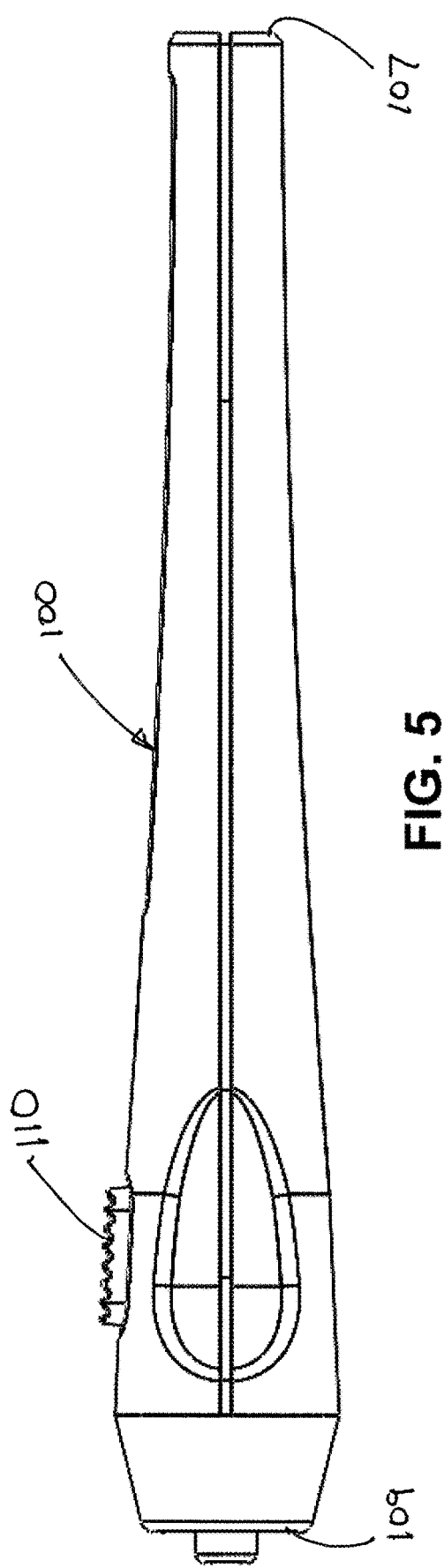
FIG. 5 is a side elevational view of a handpiece of the injection assembly illustrated in FIG. 4.

Referring to FIGS. 4-5, the handpiece 100 is a hand held element operable to provide a series of injections. The handpiece 100 comprises an elongated generally cylindrical housing 105 that forms a handle configured to be grasped by the user. The rearward end 107 of the housing 105 may taper inwardly to a minor diameter at the rearward end. The connectors for the output cable 82 and the fluid line 85 may be formed at the rearward end of the housing 105. The needle 120 projects forwardly from the forward end of the housing 105. As shown in FIG. 4, the forward end 109 of the housing 105 may include a fluid connector, such as a male Luer fitting for connecting a needle 120 mounted on a Luer hub.

The handpiece 100 may include an actuator for actuating the drive unit 20 to provide an injection. For instance, the handpiece may include a button 110. The button 110 is configured as an input device to provide an input signal to the drive unit. In particular, the button 110 may be connected with a circuit in the housing 105, such that upon actuation of the button (such as by depressing the button), the circuit transmits a signal to the drive unit. For example, upon actuation of the button, the circuit in the handpiece may provide an injection signal to the drive unit. The injection signal indicates that the drive unit should control the fluid reservoir to provide a flow of fluid from the fluid reservoir to the handpiece. As discussed further below, the drive unit may be configured to control the flow of fluid depending on the procedure. For instance, the drive unit may provide a continuous flow of fluid as long as the actuator button is actuated. Alternatively, the drive unit may provide a metered volume of fluid each time the button is actuated regardless of how long the operator depresses the button.

The fluid line 85 may be any of a variety of medical grade flexible tubing. In the present instance, the fluid line is a microbore fluid line having an internal diameter between 0.25 mm and 2.5 mm. Preferably, the microbore tubing has an internal diameter between 0.25 mm and 1.5 mm. Additionally, the length of the fluid line 85 may vary, however, preferably, the overall volume of the fluid line (which is related to both the ID and the length) is less than 2.0 mL. By using a microbore fluid line, the system reduces the priming volume of the system.

The system may also include a pressure sensing element that detects a characteristic indicative of the fluid pressure exiting the needle 120. Since increased fluid pressure during an injection can lead to patient discomfort, the system can reduce patient discomfort by reducing the fluid pressure of the fluid exiting the needle. For instance, in response to increased fluid pressure, the system may control the fluid flow to reduce the flow of fluid to the needle. Similarly, in response to reduced fluid pressure, the system may increase the fluid rate, thereby reducing the time required to complete a procedure. Alternatively, the system may utilize a generally fixed flow rate that is attenuated or reduced if the fluid pressure exceeds a predefined pressure threshold. The pressure threshold may be variable depending on the procedure.

As noted above, the system may include any of a variety of sensors for detecting a characteristic of the fluid pressure at the exit of the needle. For instance, the drive unit 20 may include a force sensor connected with the electric motor that drives the drive block 50. The sensor may be positioned at the motor output or measure the force applied by the motor to the drive mechanism, such as drive block 50. This force may then be used to determine an internal characteristic such as a force or internal pressure generated during the injection process. This characteristic may then be used as a control parameter by a microprocessor or controller to generate corresponding commands to the drive mechanism. In an exemplary embodiment, the characteristic is used to calculate an exit pressure at which fluid is ejected by the device through an elongated tube. The electric motor is then operated in such a manner that the exit pressure is maintained at or below a predetermined level to insure that a patient does not suffer pain and/or tissue damage. Alternatively, the injection assembly 80 may incorporate an inline fluid pressure sensor that detects the fluid pressure in the fluid line. The fluid pressure sensor is in electric communication with the controller of the drive unit so that the controller can control the electric motor of the drive unit to maintain the fluid pressure in the fluid line at or below a predetermined pressure to insure patient comfort. Specifically, in response to either the force sensor or the inline fluid sensor, the controller may control the drive unit to automatically reduce the flow rate of fluid until the fluid pressure is reduced below a threshold.

Referring again to FIG. 4, the injection assembly 80 includes an output cable 82. The output cable 82 connects electrical elements in the injection assembly with the drive unit 20 so that the drive unit may receive control signals from the injection assembly. In particular, a plug or jack 84 at the end of the output cable 82 mates with an input jack 75 in the drive unit to provide an electrical connection between the injection assembly 80 and the controller of the drive unit. For instance, if the injection assembly 80 includes an inline fluid pressure sensor, signals from the sensor are transmitted along the output cable to the controller of the drive unit so that the drive unit can control the flow of fluid to the needle. Similarly, if the handpiece 100 includes an actuator, such as a button 110, the electronic signals from the actuator may be communicated with the drive unit vie the output cable 84 to control the flow of fluid to the needle in response to the actuator.

Method of Operation

The following discussion describes an exemplary method of operation of the system 10 described above, which utilizes the drive unit 20 and the injection assembly 80 to perform a neurotoxin injection procedure. Such procedures are commonly done for cosmetic and therapeutic purposes and require a series of injections, often into sensitive areas.

The methodology is described in connection with a series of screen shots from the display 70 of the drive unit, as illustrated in FIGS. 6-10. In the following discussion, the display is a touch screen display so that the user can input the information using the touch screen. However, it should be understood that other input mechanisms can be provided, such as a mouse, keyboard and/or stylus.

Set-Up

Prior to injection, the operator inputs a variety of data used to control the procedure as well as to provide a record for the procedure. The system may first provide a patient data screen on the display 70, in which the operator may input various information, including, but not limited to: patient name, date of birth, date of the procedure and the name of the medical professional performing the procedure.

Figure 6:
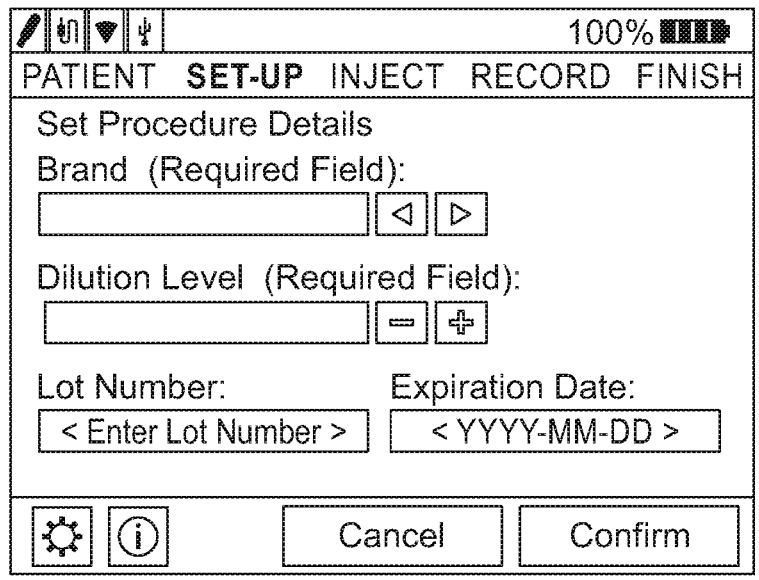
FIG. 6 is a screen shot of an operator display of the apparatus illustrated in FIG. 1, illustrating a set-up screen for a procedure using the apparatus illustrated in FIG. 1.

Referring to FIG. 6, after the patient data is entered, the user inputs data regarding the drug to be used during the procedure. In a neurotoxin injection procedure, any of a variety of neurotoxins can be used, the most common of which use a form of botulinum toxin. There are seven serotypes of botulinum toxins, including types A-G. Botulism is caused by serotypes A, B, E, F and potentially G.

The three most common brands of type A botulinum toxin commercially available are: Botox, Dysport and Xeomin. These are used to treat neck (cervical) dystonia and eye dystonia (blepharospasm) in adults in additional to multiple other neuromuscular conditions. In addition, one type B botulinum brand, Neurobloc, is also available to treat neck dystonia in adults. If patients develop immunity to one type of botulinum (either type A or type B) then sometimes the other type can be effective.

The medications have measurements that describe that amount of the active ingredient of the medication. Many medications are measured by weight (milligrams, grams, etc.). However medications that are biologically derived such as Botulinum Toxin A, are measured in units which describes the amount of effect of the medication in a given lab test. For example, Botulinum Toxin A, commercially available from Allergan as Botox® is measured in units.

The number of units of Botox administered corresponds with a therapeutic dose, and will vary from patient to patient, and procedure to procedure. As an example, the average person usually gets about 20 units of Botox to treat the lines between their brows (this number certainly varies from person to person)

Botox is available in a vial containing 100, 300 and 500 units, the most commonly used Botox has 100 units per vial. The effectiveness of the Botox on diminishing muscle movement is dependent on the dose of units given, not the dilution. The Botulinum Toxin A may be provided as a lyophilized powder. To prepare for injection, the powder is reconstituted using a diluent, such as saline, to create a solution. The volume of liquid added during the reconstitution process may vary depending on the procedure and depending on the preference of the medical professional performing the procedure. Accordingly, the volume of solution representing one unit of Botox will vary depending on the number of units in a vial and the volume of diluent added to the vial. However, during a procedure, the doctors do not rely upon fluid volume in standardization of therapeutic dosing, but instead rely upon the number of units administered to determine therapeutic dose, maximum dose and minimal dose. For instance, if a 100 unit vial of Botox is reconstituted using 4 mL of saline, each 0.1 mL of solution provides 2.5 units of Botox. Similarly, if the vial is reconstituted using 1 mL of saline, each 0.1 mL provides 10 units of Botox.

Accordingly, to prepare for the procedure, the medical professional performs the step of reconstituting the medicament with a volume of diluent. The volume of diluent and information regarding the medicament are then input into the system to calculate the volume of solution per unit of medicament. In particular, referring to FIG. 6, the user selects from a list of medicaments. Information regarding each listed medicament is stored in the memory of the drive unit. Additionally, the user inputs the dilution level for the selected medicament. For instance, the user may input the volume of diluent added. Alternatively, the system may store a list of common dilution levels, such as 1 mL per 100 unit vial, 2 mL per 100 unit vial, 2.5 mL per 100 unit vial, and 4.0 mL per 100 unit vial. In the present instance, the system stores a default dilution rate, such as 2.5 mL per 100 unit vial and allows the user to increase or decrease the dilution level by increments (such as 0.1 mL increments or 0.5 mL increments). The user also inputs information regarding the lot number so that the information can be stored with the patient record. Additionally, the user may enter the expiration date for the vial. The system may also be configured to provide a warning if the user enters a date that indicates that the vial has expired. For example if the expiration date entered by the user is before the current date (i.e. the date that the user enters the information).

Once the user has entered the information regarding the medicament and the dilution volume, the system calculates the volume of solvent for an individual unit. This calculation is made by dividing the volume of diluent by the number of units in the vial. The system stores the data regarding the calculated volume per unit to be used later to control the flow of fluid during a procedure.

The system includes circuitry for controlling the flow of fluid during different portions of a procedure. For instance, the handpiece may have a controller circuit board that enables basic functions of operation during the injection including; priming of fluid into the handpiece tubing and needle, unit dose injection, and aspiration. The hand piece may have an actuator, such as the control button 110 operable to provide additional functions, including, but not limited to flow-rate changes between different flow-rate speeds.

To prepare for a procedure, the user fills the syringe 90 with medicament from the vial prepared as described above and then attaches the syringe to the fluid line 85. The user then attaches the injections assembly 80 to the drive unit. In particular, the syringe 90 is inserted into the syringe cradle 30 of the drive unit with the push pad of the plunger engaging the drive block 50 and the discharge end of the syringe projecting from the upper end of the barrel slot 32. Additionally, the user inserts the plug 84 from the injection assembly into the jack 75 of the drive unit 20. The drive unit may include a microswitch or sensor for detecting the presence of a syringe in the syringe cradle. Accordingly, the system may display a message to the user indicative of the presence of a syringe in the cradle. Additionally, the system may not permit the procedure to continue if the sensor does not detect the presence of a syringe in the syringe cradle. Similarly, the system may include a feedback loop between the circuitry in the drive unit and the circuitry in the handpiece 100 so that when the plug is inserted into the jack 75 of the drive unit, the handpiece provides a signal to the drive unit indicative of the handpiece being attached to the drive unit. Accordingly, the drive unit may provide a signal indicative of whether the output cable is attached to the drive unit, and the system may not permit the procedure to continue if the system does not detect that the plug 84 is inserted into the jack 75.

Until the system detects that the syringe is loaded and the output cable is connected the controller locks out the drive unit so that the drive block 50 cannot be displaced. Once the two conditions are met (i.e. syringe 90 detected in syringe cradle 30 and cable 82 connected), the drive unit is enabled for expelling fluid to prime the system. The system can be primed in one of several methods. For instance, the priming volume necessary to prime the system may be known or reasonably approximated based on several known details, such as volume of the fluid line and volume of the fluid path through the handpiece. For example, in the present instance, the priming volume is approximately 0.04 mL. In such an instance, the drive unit may automatically expel an appropriate volume of fluid (e.g. 0.04 mL) from the syringe to fill the injection assembly 80 with fluid. Alternatively, in the present instance the system is primed by the user holding down an actuator, such as the button 110 on the handpiece 100. In response to the user actuating the actuator, the drive unit 20 advances the drive block 50 as long as the user actuates the actuator. Specifically, the user may continue to depress the button 110 until the user visually confirms fluid emerging from the needle 120. Once fluid emerges from the needle 120 the user releases the actuator. When the user releases the actuator, the drive unit stops advancing the drive block 50 to discontinue fluid release from the fluid reservoir.

When the user releases the actuator 110 after the priming is complete, the release of the actuator may act as a control signal. Therefore, the release of the actuator may signal to the system that the priming procedure is complete. Alternatively, in the present instance, after the user has primed the system the user may provide an input signal to the system to confirm that the injection assembly has been primed. For instance, the drive unit 20 may display an icon or other prompt on the touchscreen 70 and the user may press the icon or other prompt to provide a signal indicative of the system being primed. Once the system receives a signal indicative of the injection assembly being primed, the system moves into the injection mode to provide one or more injections as described further below.

It should be noted that the system may display a set-up screen on the touchscreen 70 showing the progress of the set-up procedure. The set-up screen may include an icon or illustration showing the mounting of the syringe in the syringe cradle and a separate icon or illustration showing the connecting of the cable 82 to the jack 75. Prior to displaying such prompts or contemporaneous with such prompts, the system may include a prompt instructing the user to include additional fluid in the syringe to be used to prime the system. For instance, the system may provide an icon or other illustration on the display indicating the amount of fluid to be added to the syringe to prime the injections assembly. Without the additional volume to be used in the priming, the number of units in the syringe after the system is primed will not match the expected number of units in the syringe before the first injection is made.

Injection Procedure

Figure 7:
FIG. 7 is a screen shot of an operator display of the apparatus illustrated in FIG. 1, illustrating a control screen for use during a procedure using the apparatus illustrated in FIG. 1.

Once the system has been set up for a procedure as described above, the medical professional may proceed with the medical procedure. Referring to FIG. 7, an injection screen is shown that may be used to control each injection during the procedure. The user selects the number of units to be injected during an injection and the flow rate to be used during the injection. Once the user has selected the number of units for an injection, and the flow rate, these values may be stored in the memory of the controller and used for each injection until the user enters different values. Alternatively, the system may be configured so that the user inputs information for each injection before the system will allow the injection.

For instance, the system may provide a menu of dosage levels for the user to select from, such as 1-5 units. Depending on the dosage level, the drive unit will calculate the volume of solution to be injected to provide the desired number of units. Additionally, the system may allow the user to select the flow rate for the injection. The system may include a list of available flow rates. Alternatively, as shown in FIG. 6, the system may include a binary choice: Comfort or Rapid. In this configuration, the "Comfort" option corresponds to a slower fluid rate, such as 0.005 mL/sec and the "Rapid" option corresponds to a faster fluid rate, such as 0.03 mL/sec. These fluid rates are only provided as exemplary rates, and it should be understood that the rates may vary. However, in the present instance, the slower fluid rate is preferably between 0.001 and 0.01 mL/sec and the faster fluid rate is preferably greater that 0.01 and less than 0.1 mL/sec.

As noted previously, the system may also include a dynamic pressure sensing capability that senses a characteristic corresponding to the fluid pressure exiting the needle. As shown in FIG. 7, the system may include a graphical display that illustrates the relative level of the detected characteristic to indicate the relative fluid pressure. In this way, the system may provide an indication to the user of a variety of conditions, including but not limited to: the position of the needle; whether the needle is obstructed; and determination of the tissue type in which the injection is performed. Pressure sensing of a specific tissue type, such as the muscle, adipose tissue, ligament or vessel can provide critical information when performing an injection to select a specific location, reduce pain and/or eliminate tissue damage. In particular, the system receives signals from the pressure sensor in real time during an injection. If the detected pressure exceeds a first pressure, a first signal is illuminated. This continues in step-wise fashion for a series of progressively higher thresholds, illuminating a different or additional signal when the next higher threshold is exceeded. In this way, the system may provide feedback to the user regarding discharge pressure during an injection.

Alternatively, the system may control the fluid flow rate for an injection in response to the fluid pressure detected during an injection. In particular, a fluid pressure threshold may be stored in the memory of the drive unit and the system will drive the fluid in response to either a pre-determined flow rate or in response to a flow rate selected by the user as described above. In response to signals received from the pressure sensor during an injection, the drive unit may attenuate the flow rate for an injection if the pressure exceeds a threshold. For instance, the drive unit may reduce the fluid flow rate to a lower fixed flow rate. Alternatively, the flow rate may reduce as the pressure increases. The correlation between the variable flow rate and the pressure may be linear or otherwise.

Accordingly, once the user selects the number of units to be injected and selects the flow rate, the user then inserts the needle 120 into the patient for a subcutaneous or intramuscular injection. Once the needle 120 is placed, the user actuates an actuator, such as the button 110 on the handpiece. In response to actuation of the actuator, the drive unit 20 automatically expels a volume of fluid from the fluid reservoir 92 through the needle. The volume of fluid is calculated to provide the desired number of units selected by the user. Additionally, the drive unit 20 controls the fluid flow to provide the desired flow rate as discussed above. In particular, the drive unit controls the rate at which drive block 50 is advanced to drive plunger 94. Additionally, the drive unit 20 controls the distance that drive block 50 is advanced based on the calculated volume of fluid to be expelled during an injection. Specifically, the drive unit 20 provides control signals to the electric motor that drives the drive block 50 to control the motor speed and the duration that the motor is actuated to thereby control the volume of fluid ejected from the syringe and the flow rate.

Once the injection is complete, the system may provide a signal to the operator indicative of the injection being completed. For instance, the system may provide an audible tone when the injection is complete or an audible tone is emitted during the entire injection process and once the injection is completed the audible tone stops. Alternatively, the system may provide an indicator of the fluid pressure in the needle 120. Therefore, the indicator will provide a signal showing that the pressure level is below a threshold corresponding to little or no fluid pressure, which is indicative of an injection being completed.

As shown in FIG. 7, the system may also provide a display indicative of the number of units remaining in the fluid reservoir 94. The system may calculate the number of units in the fluid reservoir from the data input from the user during set-up as described above. Subsequently, each time the user actuates the actuator for an injection, the system reduces the counter for the "number of units" by the number of units provided in the injection. For instance, as shown in FIG. 7, based on the user data input during set-up, the system may calculate that the fluid reservoir contains 20 units. If the user selects 1 unit as the number of units for an injection, after the user actuates the button 110, the system will increment the "Units injected" variable to 1 and will increment the "Units Remaining" variable to 19. In this way, the user can continue to provide a series of injections and specify the number of units for each injection and the system will automatically track the number of units injected and the number of units remaining so that the user will know when the fluid reservoir needs to be re-filled or replaced.

It should be understood that the system may be configured so that information that is provided visually on the LED screen can also be communicated to the user in an audible, auditory sound or in spoken words. Similarly, the handpiece may include a vibratory chip or circuit to provide data to the user via a vibratory feedback in which a vibrating electronic chip is embedded within the handpiece. In this way, the system may provide signals to the user regarding information such as delivery of the Unit Dose, the Flow-Rate, Dynamic Pressure Sensing, Obstructions or Empty Syringe, by way of example and not to be limited. The tactile, vibratory communication may include a rate of vibratory motion, pulsing or increase/decrease in the cadence of the vibration by example, further not limited to these examples.

In addition to or instead of the vibratory signals, the drive unit may include or be connected with one or more elements for providing audible signals to the user. Audible tones of varying cadence or pitch can be used to communicate the parameters of the injection, i.e., Selected Unit, Rate of Injection, Pressure Sensing data, Aspiration, Empty Syringe Condition, Obstruction of Needle and all other information that is conveyed to the screen.

Record Keeping

After completion of one or more injections, the user may proceed with a record keeping procedure that audits the procedure to account for the number of injections, the location of the injections and the number of units injected during each injection and the overall procedure. It should be understood that the user can record each injection after the completion of the individual injection. However, in the following discussion, the user records all of the injections from a series of injections after all of the injections are completed.

Figure 8:
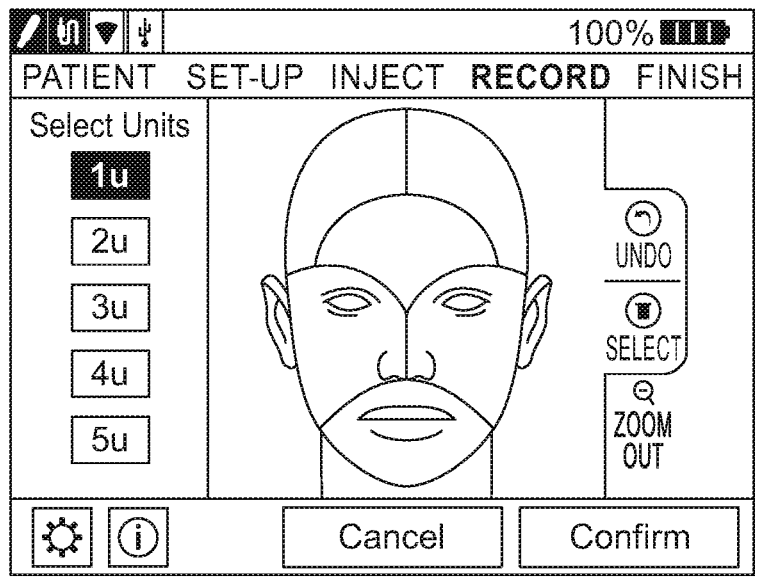
FIG. 8 is a screen shot of an operator display of the apparatus illustrated in FIG. 1, illustrating a record keeping screen for use in connection with a procedure using the apparatus illustrated in FIG. 1.
Figure 9:
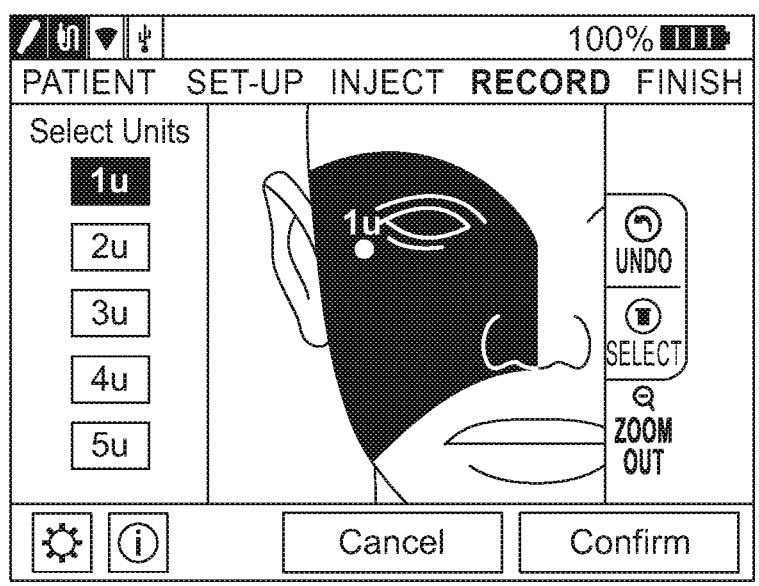
FIG. 9 is a screen shot of an operator display of the apparatus illustrated in FIG. 1, illustrating a second record keeping screen for use in connection with a procedure using the apparatus illustrated in FIG. 1.

Referring to FIGS. 8-9 the record keeping interface is illustrated. During the record keeping stage, the system provides an illustration of the area in which the injections were completed. For instance, the display 70 may display a graphical illustration of a human head. The user then selects the number of units injected for an injection and indicates the location of the injection on the graphical illustration. For instance, the user may touch the portion of the head where an injection was performed. In response, the system displays a mark, such as a dot, on the selected location. The system may also display an indication of the number of units injected next to the dot. The system also tracks the total number of units injected based on the number of units for each recorded injection. This number can then be compared against the number of injections calculated for the "Units Injected" variable as described above during the Injection Procedure. In particular, in the record keeping page may display the number of units remaining. This "Units Remaining" variable in the recording process is initially set to be equal to the "Units Injected" variable from the injection procedure. Each time the user records an injection (e.g. marks a dot on the display), the system reduces the Units Remaining variable by the number of units injected during the injection. In this way, the "Units Remaining" variable in the record keeping procedure provides a method for auditing the recorded injections so that the user can confirm the that the number of injections and the units provided is equal to the number of units provided during the series of injections.

The system may also provided enlargements of the anatomical sites to facilitate the recordation of the different injections since the injections may be provided in a small area. For instance, as shown in FIG. 8, the anatomical area may be segmented into a plurality of sub-sections. The user may select the desired sub-section by clicking on the sub-section. The system will then provide an enlarged view of the selected area as shown in FIG. 9 so that the user can more easily and accurately indicate the location of the different injections.

Figure 10:
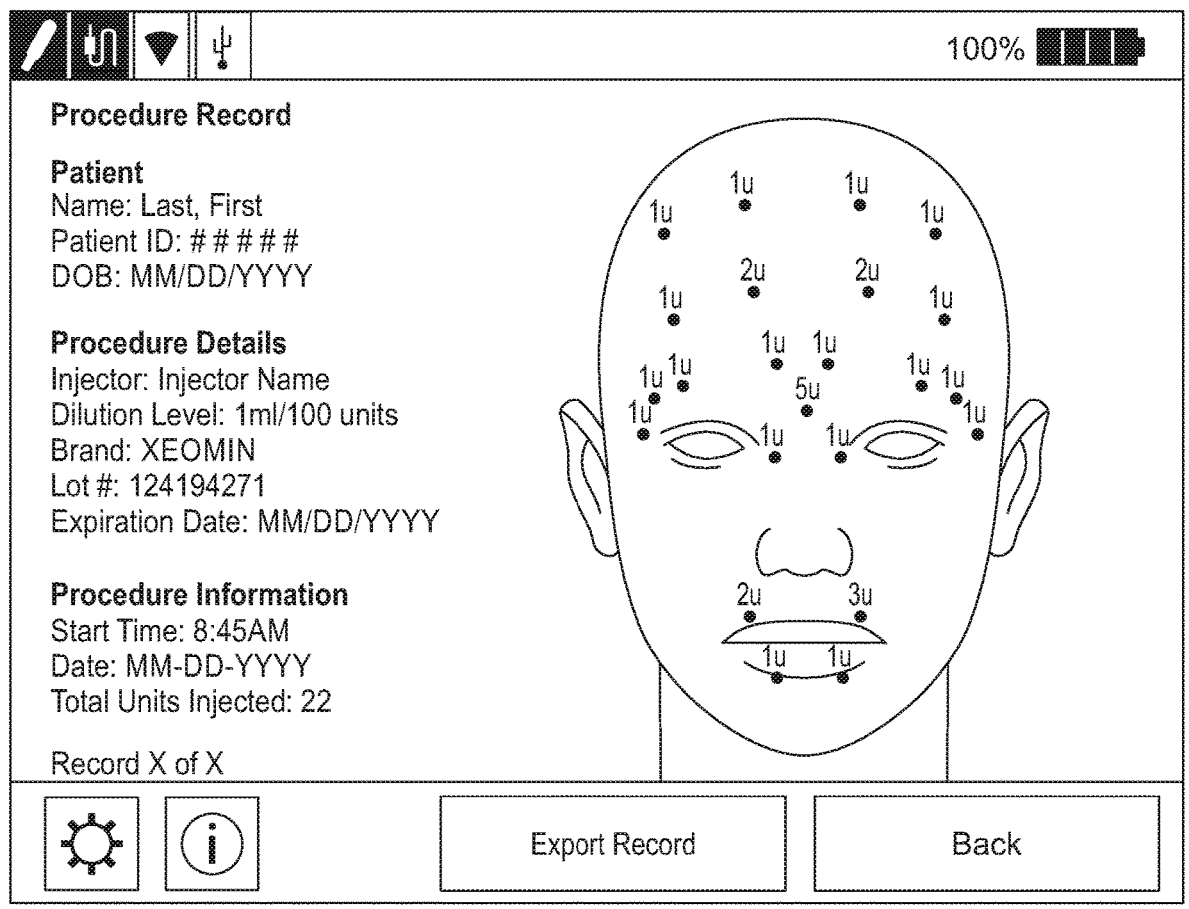
FIG. 10 is a screen shot of an operator display of the apparatus illustrated in FIG. 1, illustrating a patient record screen created in connection with a procedure using the apparatus illustrated in FIG. 1.

After the user records each injection, the system may provide a patient record that displays all of the data for the procedure, including a graphical representation of the location of each injections and the number of units injected in each injection, as well as patient data, procedure data (i.e. dilution level, medicament, lot number, expiration date, total number of units injected, procedure date and time). The patient record can be stored in a non-volatile storage device, such as a hard drive or flash drive in the drive unit. Alternatively, the drive unit may provide a data connection, whether hardwired or wireless such as Wi-Fi or blue tooth, to connect the drive unit with an external storage device such as a file server or other storage device, such as CD, DVD, magnetic drive, such as a hard drive or solid state memory, such as flash memory. Additionally or alternatively, the drive unit may be connected with a printer and the data for the patient record may be exported to the printer to print the record as shown in FIG. 10.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. An apparatus for providing an injection, comprising:
a fluid reservoir for retaining a volume of a fluid, the fluid comprising a medicament that includes a number of units of the medicament in a volume of a diluent;
a fluid controller for controlling a flow of the fluid from the fluid reservoir;
a needle in fluid communication with the fluid reservoir for injecting the medicament subcutaneously or intramuscularly into a patient;
a detector configured to detect a characteristic indicative of a fluid pressure of the fluid in the needle;
an actuator for selectively actuating the fluid controller to provide a dose of the medicament from the fluid reservoir;
wherein the fluid controller is configured to calculate a volume of fluid in the fluid reservoir required to provide the dose having a desired number of units of the medicament for the injection;
an input device for inputting information regarding a desired number of units in the dose; and
a visual display for displaying a portion of anatomy into which the needle provides a series of injections, the visual display including a record keeping interface for indicating an anatomical location of each of the series of injections, the record keeping interface indicating the number of units of medicament dispensed at the anatomical location of each of the series of injections;
wherein the fluid controller comprises a processor operable to track the number of units of the medicament dispensed during a procedure based on a number of times the actuator is actuated and information regarding the number of units of the medicament dispensed upon an actuation of the actuator, and wherein the processor is configured to compare the number of units of the medicament dispensed during the series of injections with the number of units of the medicament dispensed indicated in the record keeping interface.

2. The apparatus of claim 1, wherein the fluid controller comprises an electric motor for driving a drive element connected with the fluid reservoir to expel the fluid from the fluid reservoir.

3. The apparatus of claim 2, wherein the fluid reservoir comprises a syringe having a barrel and a plunger slidable within the barrel.

4. The apparatus of claim 3, wherein the fluid controller engages the plunger of the syringe.

5. The apparatus of claim 1, wherein the actuator is a manually actuable button.

6. The apparatus of claim 1, the apparatus further comprising a handpiece on which the needle is mounted wherein the handpiece is electronically connected with the fluid controller and the handpiece is in fluid communication with the fluid reservoir via a fluid line.

7. The apparatus of claim 6, wherein the handpiece is electronically connected with the fluid controller via a wireless connection.

8. The apparatus of claim 6, wherein the handpiece is electronically connected with the fluid controller via a wired connection.

9. The apparatus of claim 6, wherein the handpiece comprises the actuator.

10. The apparatus of claim 9, wherein the actuator comprises an actuation button.

11. The apparatus of claim 1, further comprising a detector, the detector comprising a fluid pressure sensor in line with the needle.

12. The apparatus of claim 11, wherein the fluid controller is operable to control the flow of fluid in response to signals received from the fluid pressure sensor to maintain the fluid pressure of the fluid within a range to reduce potential pain to the patient resulting from an elevated fluid pressure during the injection.

\* \* \* \* \*